(12) United States Patent
Bezuglov et al.

(10) Patent No.: US 9,408,820 B2
(45) Date of Patent: Aug. 9, 2016

(54) BRONCHOLYTIC DRUG ON THE BASIS OF PROSTAGLANDIN

(71) Applicant: OBSCHESTVO S OGRANICHENNOY OTVETSTVENNOST'YU "PROSTANIT DEVELOPMENT", Moscow (RU)

(72) Inventors: Vladimir Vilenovich Bezuglov, Moscow (RU); Igor' Viktorovich Serkov, Moskovskaya (RU)

(73) Assignee: OBSCHESTVO S OGRANICHENNOY OTVETSTVENNOST'YU "NOXI LAB" (RU)

( * ) Notice: Subject to any disclaimer, the term of this patent is extended or adjusted under 35 U.S.C. 154(b) by 6 days.

(21) Appl. No.: 14/397,092

(22) PCT Filed: Mar. 1, 2013

(86) PCT No.: PCT/RU2013/000163
§ 371 (c)(1),
(2) Date: Oct. 24, 2014

(87) PCT Pub. No.: WO2013/162416
PCT Pub. Date: Oct. 31, 2013

(65) Prior Publication Data
US 2015/0141505 A1    May 21, 2015

(30) Foreign Application Priority Data
Apr. 24, 2012   (RU) ................................ 2012116226

(51) Int. Cl.
*A61K 31/21*   (2006.01)
*A61K 31/20*   (2006.01)

(52) U.S. Cl.
CPC ................. *A61K 31/21* (2013.01); *A61K 31/20* (2013.01)

(58) Field of Classification Search
CPC ...................................................... A61K 31/21
USPC .................................................. 514/509, 573
See application file for complete search history.

(56) References Cited

PUBLICATIONS

International Search Report, PCT/RU2013/000163, Sep. 26, 2013.
Gail M. Gauvreau et al., "Protective Effects of Inhaled PGE2 on Allergen-Induced Airway Responses and Airway Inflammation", American Journal of respiratory and Critical Care Medicine, 1999, vol. 159, pp. 31-36.
Serkov I.V. et al., Mnogofunktionalnye soedineniya, sonderzhashchie organicheskie nitraty,—prototipy gibridnykh lekarstvennykh preparatov, Uspekhi Khimii, 2009, No. 78(5), pp. 42-465.
Lipin-instruktsiya po primeniiu, NIFP, Kiev, Nov. 18, 1991, Retrieved from Internet: URL: http://www.ifp.kiev.ua/doc/metod-doc/lipin.htm.

*Primary Examiner* — Raymond Henley, III
(74) *Attorney, Agent, or Firm* — Matthew A. Pequignot; Pequignot + Myers LLC

(57) ABSTRACT

The invention relates to the field of medicine, and specifically to pulmonology, and concerns a method for treating inflammatory and obstructive diseases of the airways, in particular bronchial asthma and obstructive bronchitis, with the aid of a drug on the basis of 1',3'-dinitroglycerol ester 11(S),15(S)-dihydroxy-9-keto-5Z,13E-prostadienoic acid (nitroproston) having a marked bronchodilatory effect. The present invention provides for an expansion of the range of broncholytic drugs by the use of a derivative of natural prostaglandin $E_2$, which is characterized by greater biological activity and the absence of noticeable side effects.

16 Claims, 1 Drawing Sheet

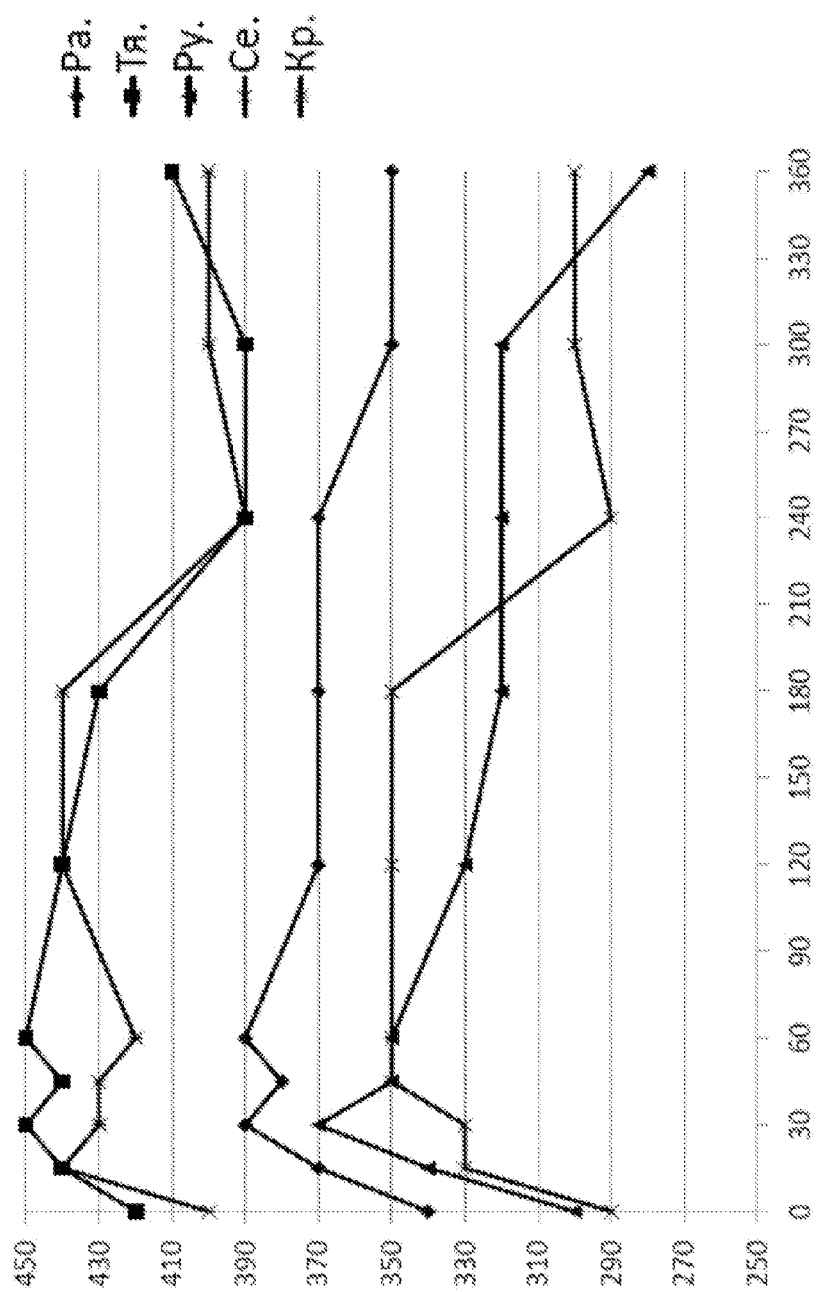

BRONCHOLYTIC DRUG ON THE BASIS OF PROSTAGLANDIN

RELATED APPLICATION DATA

This application is the national stage entry of International Appl. No. PCT/RU2013/000163, filed Mar. 1, 2013, which claims priority to Russian Patent Application No. RU 2012116226, filed Apr. 24, 2012. All claims of priority to these applications are hereby made, and each of these applications is hereby incorporated in its entirety by reference.

FIELD OF THE INVENTION

The present invention relates to the field of medicine, namely, pulmonology, and concerns the treatment of inflammatory or obstructive respiratory diseases, especially asthma and obstructive bronchitis by using a drug that contains the active ingredient with expressed bronchial dilatory effect.

BACKGROUND OF THE INVENTION

Currently only three types of drugs (except that corticosteroids, which have anti-inflammatory effects): agonists of beta-adrenergic receptors (rapid and prolonged action); cholinolytics (muscarinic receptor antagonists); Theophylline (a derivative of purine) are used in therapy of asthma and other bronchial obstructive diseases.

In addition, the therapy schema is now included the regular use of inhaled corticosteroids alone or in combination with long-acting beta-agonists. However, despite such seemingly effective remedies, about half of patients with asthma is poorly responding to the therapy. Another problem is acute attacks of asphyxia. The ability of these drugs to stop the asthma attack for patients with a long history of the use of long acting beta-agonists is diminished. One of the solution the problem of expansion of the arsenal of broncholytic drugs is to exploit an alternative pharmacological targets.

Known is the bronchial dilating effect of natural prostaglandin E2, mediated by its interaction with the second subtype EP-receptors (X. Norel, L. Walch, C. Labat, J-P. Gascard, E. Dulmet, C. Brink. Prostanoid receptors involved in the relaxation of human bronchial preparations.//British Journal of Pharmacology (1999) 126, 867-872), which is observed as in experiments in vitro on isolated strips of bronchus, as in vivo experiments on laboratory animals. However, the use of natural prostaglandin E2 to cut off bronchoconstriction in individuals is not possible because of the strong cough reflex.

The task of elimination of this side effect has been solved by the authors of this invention by modification of molecules of prostaglandin by introducing an additional fragment containing the nitro group, namely by obtaining 1',3'-dinitroglycerol ester of 11(S),15(S)-dihydroxy-9-keto-5Z,13E-prostadienoic acid—derivative of natural prostaglandin E2, named nitroproston. How to prepare nitroproston and spectrum of its activity in the smooth muscle experiments have been described by the authors of this invention in the earlier patent of RU 2067094. In experiments on relaxation of the guinea pig trachea a value EC50 $0.007\pm0.025$ mkM for nitroproston vs $0.14\pm0.08$ mkM—for natural prostaglandin E2 was obtained, demonstrating considerably more significant activity of nitroproston compared to the natural prostaglandin. However, as with natural prostaglandin E2, the data collected on the smooth muscle of experimental animals, did not permits to make a conclusion on the suitability of the substance as a bronchial dilating drug for the application in humans. The authors conducted additional research on healthy volunteers and patients with bronchial asthma, to demonstrate the effectiveness of application of nitroproston as a broncholytics in humans, that does not cause noticeable side effects.

SUMMARY OF THE INVENTION

The present invention solves the task of creating of bronchial dilating drug on the basis of 1',3'-dinitroglycerol ester of 11(S),15(S)-dihydroxy-9-keto-5Z,13E-prostadienoic acid (nitroproston). This drug is any form of nitroproston suitable for introduction into the respiratory tract by inhalation, for example in the form of isotonic solution. In experiments on a limited group of volunteers with asthma in the phase of unstable remission and expressing registered bronchospasm nitroproston in the form of isotonic solution (in a dose of 7.5 micrograms per inhalation) caused prolonged dilation of bronchus without side effects. There have been registered no cough bouts either in patients with asthma, neither in healthy volunteers. The only side effect of inhalation solution of nitroproston was transient dry mouth. Studies have shown that nitroproston in therapeutic doses (5-20 µg per inhalation) is non-toxic, does not cause a reaction from other human body organs. Therapeutic index measured in rodents is greater than 15000.

Thus, the claimed compound solves the problem of expansion of nomenclature of bronchodilators and can be used in medicine to cure asthma attacks and other bronchial obstructive diseases.

One of the objects of the present invention is a drug intended for the treatment of inflammatory or obstructive respiratory diseases, especially asthma and obstructive bronchitis.

The introduction of the above drug is preferably performed through inhalation, i.e. the active component is in a form suitable for inhalation. The form of the drug, intended for inhalation, i.e. containing the active ingredient can be, for example, the composition for fine disperse spray such as spray containing the active ingredient in the form of a solution or dispersion in propellant, or disperse composition, contains the active substance in water, organic or aqueous/organic medium. For example, the form for inhalation of the drug may be a spray containing the active ingredient in the form of a solution or dispersion in propellant.

In particular, the drug of this invention may be prepared in a form of alcohol solution of the active substance. In order for such solution to be suitable for use as a spray, to this does not necessarily add liquefied petroleum gas, such as norfluran (1,1,1,2-tetrafluoroethane).

In a preferred embodiment of the drug is a solution of 1',3'-dinitroglycerol ester of 11(S),15(S)-dihydroxy-9-keto-5Z,13E-prostadienoic acid in the physiological solution, suitable for inhalations.

Another object of the present invention is a method of treating inflammatory or obstructive respiratory diseases such as asthma and obstructive bronchitis. To this end patient who is in need of such treatment, is introduced effective amount of 1',3'-dinitroglycerol ester of 11(S),15(S)-dihydroxy-9-keto-5Z,13E-prostadienoic acid.

In a preferred embodiment of the present invention 1',3'-dinitroglycerol ester of 11(S),15(S)-dihydroxy-9-keto-5Z, 13E-prostadienoic acid is administered to a patient in the form of isotonic solution, which is produced by dissolving the active component in physiological solution desired volume.

In another preferred embodiment of the present invention the therapeutically effective amount 1',3'-dinitroglycerol ester of 11(S),15(S)-dihydroxy-9-keto-5Z,13E-prostadienoic acid in the above prepared solution, which is administered to the patient, for example by inhalation, can range from 5 to 20 micrograms (μg).

In the most preferred embodiment of the present invention 1',3'-dinitroglycerol ester of 11(S),15(S)-dihydroxy-9-keto-5Z,13E-prostadienoic acid is administered to the patient by inhalation in an amount from 5 to 7.5 μg per inhalation.

In those cases the implementation of this invention when a single injection of 1',3'-dinitroglycerol ester of 11(S),15(S)-dihydroxy-9-keto-5Z,13E-prostadienoic acid is not enough to achieve the desired result, in order to enhance the therapeutic effect and its prolongation in time, the repeated introduction of the active ingredient in the form of inhalation can be applied to a patient.

Another object of this invention is the use of 1',3'-dinitroglycerol ester of 11(S),15(S)-dihydroxy-9-keto-5Z,13E-prostadienoic acid as a bronchial dilating agent. Also 1',3'-dinitroglycerol ester of 11(S),15(S)-dihydroxy-9-keto-5Z,13E-prostadienoic acid can be used to prepare the drug product intended for the treatment of inflammatory or obstructive respiratory diseases such as asthma and obstructive bronchitis.

BRIEF DESCRIPTION OF THE DRAWINGS

The FIG. 1 shows the change in peak volumetric rate of exhalation within 360 minutes after nitroproston inhalation in a dose of 7.5 micrograms (μg). On the x-axis is the time after the introduction of the nitroproston, min; on the y-axis is the peak exhale velocity (l/min). The names of patients are abbreviated.

DETAILED DESCRIPTION OF THE INVENTION

The following examples illustrate the embodiment of this invention.

Example 1

Synthesis of 1',3'-dinitroglycerol ester of 11(S),15 (S)-dihydroxy-9-keto-5Z,13E-prostadienoic acid (nitroproston)

In the mixture of 125 ml toluene and 20 ml dry acetone at constant stirring in argon atmosphere one gram (2.8 mM) of prostaglandin E2 was dissolved and was consistently added 1.46 g (14.46 mM) triethylamine and 2 g (10.47 mM) p-toluenesulfonyl chloride and this was stirred 10 min. Then to the resulting solution of mixed anhydride 1 g (8.2 mM) dimetylaminopyridine and 1.5 g (8.24 mM) 1.3-glycerol dinitrate were added and the resulting mixture was stirred for 1 h at 25° C. Triethylamine hydrochloride was off-filtered, filtrate was evaporated under reduced pressure up to half, the amount of triethylamine hydrochloride that fell was off-filtered again, and the filtrate was put onto the column with 200 g of silica gel L (100-250 μm) and the column was elute with a gradient system of benzene-acetone. Fractions containing product (check using TLC) were combined, the solvent was evaporated under reduced pressure. It was received 995 mg of nitroproston, yield 68% as viscous, colorless oil, $R_f$ 0.39 (benzene-dioxane-acetic acid, 40:10:1), $[\alpha]_D^{20}$ −42.1° (c=1, ethanol), mass-spectrum (m/z): 517 (M+H). Mass-spectrum (chemical ionization), (m/z, %): 533 (M+$NH_3$, 69), 516 (M, 60), 489 (M+H—CO, 40), 471 (M+H—$NO_2$, 29), 426 (M-× 2×$NO_2$, 100), 409 (M-2×$NO_2$—OH, 69), 391 (M-2×$NO_2$—OH—$H_2O$, 58), 352 (M-($CH_2ONO_2$)$_2$C, 54), 334 (M-($CH_2ONO_2$)$_2$COH, 44), 317 (M-($CH_2ONO_2$)$_2$COH—$H_2O$, 86). IR-spectrum, (KBr, $nm^{-1}$: 3400 (OH), 2860-3100 (CH). 1750 (C=O), 1660 (N=O, asym), 1280 (N=O, sym), 860 (O—N), 980 (C—C), 1158, 1102, 1074, 1010, 754, 634. $^1$H NMR (500 MHz, $CDCl_3$, δ, ppm): 5.59 (1H, dd, J=7.5 Hz, J=15 Hz, H-14), 5.49 (1H, dd, J=8.5 Hz, J=15 Hz, H-13), 5.35 (3H, m, H-5, H-6, H-22), 4.74 (2H, dd, J=4 Hz, J=12.5 Hz, H-21 or H-23), 4.56 (2H, dd, J=6 Hz, J=12.5 Hz, H-21 or H-23), 4.03 (1H, q, J=7 Hz, H-15), 3.99 (1H, q, J=8.5 Hz, H-11), 2.67 (1H, dd, J=7 Hz, J=18 Hz, H-1013), 2.34 (2H, t, J=7 Hz, H-2), 2.29 (2H, m, H-12, H-10α), 2.08 (5H, m, H-8, H-3. H-7), 1.67 (2H, dq, J=2 Hz, J=7 Hz, H-16), 1.52 (2H, dm, H-4), 1.31 (6H, m, H-17, H-18, H-19), 0.90 (3H, t, J=7 Hz, H-20). $^{13}$C-NMR (500 MHz, $CDCl_3$, δ, ppm): 211.75 (C-9), 171.31 (C-1), 136.59 (C-22), 131.31 (C-14), 130.04 (C-13), 127.99 (C-5), 126.90 (C-6), 73.07 (C-15), 72.16 (C-11), 69.59 (C-21 or C-23), 66.54 (C-21 or C-23), 54.79 (C-12), 54.13 (C-8), 46.23 (C-10), 37.76 (C-16), 33.45 (C-2), 32.26 (C-18), 26.88 (C-4), 25.75 (C-7), 25.52 (C-17), 24.89 (C-3), 23.25 (C-19), 14.87 (C-20).

The solution of nitroproston in ethanol in an appropriate concentration was prepared. The standard solution had a concentration of 10 mg per mL (1 percent).

Example 2

Determination of the Acute Toxicity and Therapeutic Index of Nitroproston

Experiments conducted on white outbred male mice (22±2 g weight). Nitroproston in the form of alcohol solution was injected intraperitoneal to the 10 mice in a maximum of 50 μl per dose of 215 mg/kg. The control group (10 animals) was injected with the same volume of pure ethyl alcohol. Animal health monitoring period was 14 days. Therapeutic index defined as the ratio of LD50 values (toxic dose) to the ED20 for change in blood pressure (pharmacological dose). And in the control and experimental group animal deaths have not observed. Thus, one can consider that a) nitroproston in the form of alcohol solution is low-toxic compound; b) therapeutic index for nitroproston is above 15000.

Example 3

Determination of Toxicity of Nitroproston in Repeated Introduction

Experiments conducted on white outbred male mice (22±2 g weight). Animals were divided into three groups of 10 animals each. Nitroproston (1% of alcoholic solution) was diluted with water and was injected in the volume 20 μl in two doses: 50 and 500 μg/kg. The control group was injected with equal volume of distilled water. The injections worked every day for 14 days. The animals were observed daily, measuring their weight, the intake of food and water. There have been observed no differences in the state and behavior of the animals between the control and experimental groups. Thus, it was established that the introduction of nitroproston for 14 days at doses of 50 and 500 μg/kg has no toxic effects.

Example 4

Bronholytic Activity of Nitroproston

The tests were carried out on healthy volunteers (average age 42.6±3.9 years) and patients with bronchial asthma in unstable remission state (average age 48.3±5.1 years). Nitroproston was introduced via inhalation in the form of a solution in the physiological solution in doses of 5 and 7.5 μg per inhalation. To a person skilled in the art will not meet a difficulty to prepare the solution for inhalation, knowing the dose of the active substance and the volume of the solution, which will be determined by technical features used in the specific context of the inhaler. For all patients test with Berotec (standard bronchial dilatatory drug) gave a positive result, indicating presence of bronchospasm. External respiratory function was determined with the help of automatic spiroanalyzer (VI 8911, Estonia). In healthy volunteers, neither Berotec or nitroproston did not cause significant changes in the functions of the external respiration. In patients who have received a dose of 5 μg of nitroproston per inhalation parameters of external breath have improved slightly, but they have not noticed any side effects. All patients who have received a dose of 7.5 μg of nitroproston per inhalation, external respiration indices have been improved. So, change the maximum 25% volume exhalation velocity ranged from 10.4 to 32.2% as compared to the original values. Changes in peak volumetric velocity of exhalation in patients who have received 7.5 micrograms nitroproston per inhalation, are presented at the FIG. 1. All patients responded by the strongest increase of this parameter, reflecting on the effectiveness of nitroproston as a bronchodilator for the treatment of inflammatory or obstructive lung disease in humans.

The invention claimed is:

1. A drug for the treatment of inflammatory or obstructive diseases of the respiratory tract, containing as a bronchial dilating matter an effective amount of active component of 1',3'-dinitroglycerol ester of 11(S),15(S)-dihydroxy-9-keto-5Z,13E-prostadienoic acid and pharmaceutically acceptable carriers or diluents.

2. The drug according to claim 1, wherein the inflammatory or obstructive airway disease is selected from the group consisting of bronchial asthma and obstructive bronchitis.

3. The drug according to claim 1, which is in a form suitable for inhalation.

4. The drug according to claim 3, which is a solution of the active component in the physiological solution.

5. A method of treating inflammatory or obstructive diseases of the respiratory tract, which includes administration to a patient who needs of such treatment, the effective amount of 1',3'-dinitroglycerol ester of 11(S),15(S)-dihydroxy-9-keto-5Z,13E-prostadienoic acid as a bronchial dilating drug.

6. The method according to claim 5, wherein the inflammatory or obstructive airway disease is selected from the group consisting of bronchial asthma and obstructive bronchitis.

7. The method according to claim 5, wherein the 1',3'-dinitroglycerol ester of 11(S),15(S)-dihydroxy-9-keto-5Z,13E-prostadienoic acid administered to the patient by inhalation.

8. The method according to claim 7, wherein the 1',3'-dinitroglycerol ester of 11(S),15(S)-dihydroxy-9-keto-5Z,13E-prostadienoic acid administered to the patient in the form of a solution in the physiological solution.

9. The method according to claim 7, wherein the amount of 1',3'-dinitroglycerol ester of 11(S),15(S)-dihydroxy-9-keto-5Z,13E-prostadienoic acid, delivered to a patient is in the range from 5 up to 20 μg per inhalation.

10. The method according to claim 9, wherein the amount of 1',3'-dinitroglycerol ester of 11(S),15(S)-dihydroxy-9-keto-5Z,13E-prostadienoic acid, being delivered to a patient is in the range from 5 to 7.5 μg per inhalation.

11. The method according to claim 5, wherein to a patient in need of such treatment, is repeatedly administered of the effective amount of 1',3'-dinitroglycerol ester of 11(S),15(S)-dihydroxy-9-keto-5Z,13E-prostadienoic acid.

12. The method according to claim 6, wherein to a patient in need of such treatment, is repeatedly administered of the effective amount of 1',3'-dinitroglycerol ester of 11(S),15(S)-dihydroxy-9-keto-5Z,13E-prostadienoic acid.

13. The method according to claim 7, wherein to a patient in need of such treatment, is repeatedly administered of the effective amount of 1',3'-dinitroglycerol ester of 11(S),15(S)-dihydroxy-9-keto-5Z,13E-prostadienoic acid.

14. The method according to claim 8, wherein to a patient in need of such treatment, is repeatedly administered of the effective amount of 1',3'-dinitroglycerol ester of 11(S),15(S)-dihydroxy-9-keto-5Z,13E-prostadienoic acid.

15. The method according to claim 9, wherein to a patient in need of such treatment, is repeatedly administered of the effective amount of 1',3'-dinitroglycerol ester of 11(S),15(S)-dihydroxy-9-keto-5Z,13E-prostadienoic acid.

16. The method according to claim 10, wherein to a patient in need of such treatment, is repeatedly administered of the effective amount of 1',3'-dinitroglycerol ester of 11(S),15(S)-dihydroxy-9-keto-5Z,13E-prostadienoic acid.

* * * * *